(12) United States Patent
Pesaro et al.

(10) Patent No.: US 9,417,252 B2
(45) Date of Patent: *Aug. 16, 2016

(54) METHOD FOR THE DETECTION OF PROVENTRICULAR DILATATION DISEASE AND KIT THEREOF

(71) Applicant: UNIVERSITA' DEGLI STUDI DI CAMERINO, Camerino (MC) (IT)

(72) Inventors: Stefano Pesaro, Trieste (IT); Giacomo Rossi, Pisa (IT)

(73) Assignee: UNIVERSITÀ DEGLI STUDI CAMERINO, Camerino (MC) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/735,286

(22) Filed: Jun. 10, 2015

(65) Prior Publication Data

US 2015/0285826 A1    Oct. 8, 2015

Related U.S. Application Data

(63) Continuation of application No. 13/119,078, filed as application No. PCT/IB2009/053892 on Sep. 7, 2009, now Pat. No. 9,081,025.

(30) Foreign Application Priority Data

Sep. 17, 2008    (IT) .............................. RM2008A0497

(51) Int. Cl.
*G01N 31/00* (2006.01)
*G01N 33/53* (2006.01)
*G01N 33/92* (2006.01)

(52) U.S. Cl.
CPC .......... *G01N 33/92* (2013.01); *G01N 2333/465* (2013.01); *G01N 2405/10* (2013.01); *G01N 2800/06* (2013.01)

(58) Field of Classification Search
CPC ..... A61K 35/30; A61K 38/00; A61K 38/179; A61K 2300/00; C07K 16/18
See application file for complete search history.

(56) References Cited

U.S. PATENT DOCUMENTS 9,081,025 B2 * 7/2015 Rossi ..................... G01N 33/92

FOREIGN PATENT DOCUMENTS

WO    WO 2004/087173    10/2004

OTHER PUBLICATIONS

International Search Report for PCT/IB2009/053892, May 6, 2010.
Rossi, G. et al., "Parrot proventricular dilation disease", The Veterinary Record, vol. 163, No. 10, (Sep. 6, 2008), pp. 310.
Kistler, K.L. et al., "Recovery of divergent avian bornaviruses from cases of proventricular dilatation disease: identification of a candidate etiologic agent", Virology Journal 2008, vol. 5, (Jul. 31, 2008), p. 88 (pp. 1-15).
Bole, K., "UCSF researchers identify virus behind mysterious parrot disease", UCSF News Office, [Online], (Jul. 29, 2008), 2 pages.
Panzetta, P. et al., "Ganglioside expression during differentiation of chick retinal cells in vitro", Neurochemical Research, vol. 25, No. 1, (Jan. 2000), pp. 163-169.
Rossi, G. et al., "Parrot proventricular dilatation disease: a possible model of Guillain-Barre syndrome?", Nature Precedings, vol. hd1:10101/npre.2008.2590.1, (Dec. 2, 2008), [Online], 2 pages.
Seybold, U. et al., "Brain gangliosides in birds with different types of postnatal development (nidifugous and nidicolous type)", Developmental Brain Research, vol. 17, No. 1-2, (Jan. 1, 1985), pp. 201-208.
Freischutz, B. et al., "Unusual gangliosidosis in emu (*Dromaius novaehollandiae*)", Journal of Neurochemistry May 1997 LNKD-PUBMED:9109534, vol. 68, No. 5, (May 1997), pp. 2070-2078.
Alaedini et al., "Ganglioside Agglutination Immunoassay for Rapid Detection of Autoantibodies in Immune-Mediated Neuropathy", Journal of Clinical Laboratory Analysis, vol. 15, (2001) pp. 96-99.
Asbury et al., "Assessment of Current Diagnostic Criteria for Guillain-Barré Syndrome", Annals of Neurology, vol. 27, (1990) pp. S21-S24.
Bech et al., "IgM anti-GM1 antibodies in the Guillain-Barré syndrome: a serological predictor of the clinical course", Journal of Neuroimmunology, vol. 72, (1997) pp. 59-66.
Belkum et al. "A *Campylobacter jejuni* gene associated with immune-mediated neuropathy" Nature Medicine, vol. 7, No. 7 (Jul. 2001) pp. 752-753.
Berhane et al., "Peripheral neuritis in psittacine birds with proventricular dilatation disease", Avian Pathology, vol. 30 (2001) pp. 563-570.
Bond et al., "Screening for Psittacine Proventricular Dilatation Syndrome", Proceedings Association of Avian Veterinarians (1993) pp. 92-97.
Carpo et al., Anti-$GD_{1a}$ Ganglioside Antibodies in Peripheral Motor Syndromes, Annals of Neurology, vol. 39, No. 4 (Apr. 1996) pp. 539-543.
Carpo et al., "Clinical correlate and fine specificity of anti-GQ1b antibodies in peripheral neuropathy" Journal of Neurological Sciences, vol. 155, (1998) pp. 186-191.
Carpo et al., "Clinical presentation and outcome of Guillain-Barré and related syndromes in relation to anti-ganglioside antibodies", Journal of Neurological Sciences, vol. 168, (1999) pp. 78-84.
Cazayoux-Vice, "Myocarditis as a Component of Psittacine Proventricular Dilatation Syndrome in a Patagonian Conure", Avian Diseases, vol. 36 (1992) pp. 1117-1119.
Chiba et al., "Serum anti-$GQ_{1b}$, IgG antibody is associated with ophthalmoplegia in Miller Fisher syndrome and Guillain-Barré syndrome: Clinical and immunohistochemical studies", Neurology, vol. 43 (Oct. 1993) pp. 1911-1917.

(Continued)

*Primary Examiner* — Lisa Cook
(74) *Attorney, Agent, or Firm* — Nixon & Vanderhye P.C.

(57) ABSTRACT

A ganglioside or a mixture of gangliosides, isolated from the peripheral and central nervous system of a bird, in particular a parrot, their use for the preparation of a medicament, methods for the diagnosis of Proventricular Dilatation Disease and diagnostic kits thereof, are disclosed.

3 Claims, No Drawings

(56) References Cited

OTHER PUBLICATIONS

Clark, "Proventricular Dilatation Syndrome in Large Psittacine Birds" Avian Diseases, vol. 28, No. 3, (1984), pp. 813-815.
Dabby et al., "Antisulfatide antibodies in neuropathy" Neurology, vol. 54 (2000) pp. 1448-1452.
Degernes et al., "Proventricular Dilatation Syndrome in a Green-Winged Macaw", Proceedings Association of Avian Veterinarians, (1991) pp. 45-50.
Dullforce et al., "Enhancement of T cell-independent immune responses in vivo by CD40 antibodies" Nature Medicine, vol. 4, No. 1 (Jan. 1998) pp. 88-91.
Gough et al., "Virus-like particles associated with macaw wasting disease" The Veterinary Record, (Jul. 6, 1996) p. 24.
Graham et al., "Wasting/Proventricular Dilation Disease", Proceedings Association of Avian Veterinarians, (1991) pp. 43-44.
Graham DL., "Infiltrative splanchnic Neuropathy a Component of the "Wasting Macaw" Complex?", Proc Internatl Conf Avian Med (1984) pp. 275-280.
Gregory et al., "Investigations of Eastern Equine Encephalomyelitis Virus as the Causative Agent of Psittacine Proventricular Dilatation Syndrome", Journal of Avian Medicine and Surgery, vol. 11, No. 3, (1997) pp. 187-193.
Gregory et al., "A Review of Proventricular Dilatation Syndrome", Journal of the Association of Avian Veterinarians, vol. 8, No. 2, (1994) pp. 69-75.
Gregory et al., "Histologic evaluation of the crop for diagnosis of proventricular dilatation syndrome in psittacine birds" J Vet Diagn Invest., vol. 8 (1996) pp. 76-80.
Ho et al., Guillain-Barré syndrome in northern China, Relationship to Campylobacter jejuni infection and anti-glycolipid antibodies, Brain, vol. 118 (1995) pp. 597-605.
Ho et al., "Anti-GD1a Antibody is Associated with Axonal But Not Demyelinating Forms of Guillain-Barré Syndrome", Annals of Neurology, vol. 45, No. 2 (Feb. 1999) pp. 168-173.
Hughes et al., "Pathogenesis of Guillain-Barré syndrome", Journal of Neuroimmunology, vol. 100 (1999) pp. 74-97.
Ilyas et al., "Antibodies to GT1a ganglioside in patients with Guillain-Barré syndrome", Journal of Neuroimmunology, vol. 82 (1998) pp. 160-167.
Ilyas et al., "Antibodies of sulfated glycolipids in Guillain-Barré syndrome", Journal of the Neurological Sciences, vol. 105 (1991) pp. 108-117.
Joyner et al., "Encephalitis, Proventricular and Ventricular Myositis, and Myenteric Ganglioneuritis in an Umbrella Cockatoo", Avian Diseases, vol. 33 (1989) pp. 379-381.
Koga et al., "Range of cross reactivity of anti-GM1 IgG antibody in Guillain-Barré syndrome" J. Neurol. Neurosurg. Psychiatry, vol. 71 (2001) pp. 123-124.
Kuwabara et al., "IgG Anti-GM1 Antibody is Associated with Reversible Conduction Failure and Axonal Degeneration in Guillain-Barré Syndrome", Annals of Neurology, vol. 44, No. 2 (Aug. 1998) pp. 202-208.
Lutz et al., "Psittacine proventricular dilatation syndrome in an Umbrella cockatoo", JAVMA, vol. 198, No. 11 (Jun. 1, 1991) pp. 1962-1964.
Mannl et al., "Neuropathic Gastric Dilatation in Psittaciformes", Avian Diseases, vol. 31, No. 1 (1987) pp. 214-221.
Odaka et al., "Anti-GQ1b IgG antibody syndrome: clinical and immunological range", J. Neurol Neurosurg Psychiatry, vol. 70 (2001) pp. 50-55.
Ogawara et al., "Axonal Guillain-Barré Syndrome: Relation to Anti-Ganglioside Antibodies and Campylobacter jejuni Infection in Japan", Annals of Neurology, vol. 48, No. 4 (Oct. 2000) pp. 624-631.
Ogino et al., "IgG anti-GM1 antibodies from patients with acute motor neuropathy are predominantly of the IgG1 and IgG3 subclasses", Journal of Neuroimmunology, vol. 58 (1995) pp. 77-80.
Phalen, "An Outbreak of Psittacine Proventricular Dilatation Syndrome (PPDS) in a Private Collection of Birds and an Typical Form of PPDS in a Nanday Conure", Ann Conf Assoc Vet, (1986) pp. 27-34.
Press et al., "Temporal profile of anti-ganglioside antibodies and their relation to clinical parameters and treatment in Guillain-Barré syndrome", Journal of the Neurological Sciences, vol. 190 (2001) pp. 41-47.
Rich, "Classic and Atypical Cases of Proventricular Dilatation Disease", Proceedings Association of Avian Veterinarians, (1992) pp. 119-125.
Ridgway et al., "Proventricular Dilatation in Psittacines", Proc Ann Conf Assoc Avian Vet, (1983) pp. 228-230.
Rosskopf et al., "Pet Avian Disease Syndromes", Proc Ann Conf Assoc Avian Vet, (1985) pp. 295-317.
Rosskopf et al., "Pet Avian Conditions and Syndromes—An Update", Proc Ann Conf Assoc Avian Vet, (1986) pp. 377-400.
Spenser et al., "Common Infectious Diseases of Psittacine Birds Seen in Practice", Veterinary Clinics of North America: Small Animal Practice, vol. 21, No. 6 (Nov. 1991) pp. 1213-1230.
Suedmeyer, "Diagnosis and Clinical Progression of Three Cases of Proventricular Dilatation Syndrome", Journal of the Association of Avian Beterinarians, vol. 6, No. 3 (1992) pp. 159-163.
Uncini et al., "Fisher Syndrome with Tetraparesis and antibody to GQ1b: Evidence for Motor Nerve Terminal Block", Muscle & Nerve, vol. 22 (May 1999) pp. 640-644.
Willison et al., "Immunoglobulin subclass distribution and binding characteristics of anti-GQ1b antibodies in Miller Fisher syndrome", Journal of Neuroimmunology, vol. 50 (1994) pp. 159-165.
Woerpel et al., "Proventricular Dilatation and Wasting Syndrome: Myenteric Ganglioneuritis and Encephalomyelitis of Psittacines; an Update." Proc Internatl Conf Avian Med (1984) pp. 25-28.
Yako et al., "Serum antibody against a peripheral nerve myelin ganglioside, LM1, in Guillain-Barré syndrome", Journal of the Neurological Sciences, vol. 168 (1999) pp. 85-89.
Yuki et al., "Close association of Guillain-Barré syndrome with antibodies to minor monosialogangliosides GM1b and GM1α", Journal of Neuroimmunology, vol. 74 (1997) pp. 30-34.
Verified Translation of Priority Document: Italian Application N. RM2008A000497; filed on Sep. 17, 2008; 11 pages.
Rossi et al. (The Veterinary Record, vol. 163, No. 10, Sep. 6, 2008, p. 310).

\* cited by examiner

METHOD FOR THE DETECTION OF PROVENTRICULAR DILATATION DISEASE AND KIT THEREOF

CROSS REFERENCE

This application is a continuation of application Ser. No. 13/119,078, filed Mar. 15, 2011, now U.S. Pat. No. 9,081,025, which is the U.S. national phase of International Application No. PCT/IB2009/053892 filed Sep. 7, 2009 which designated in the U.S. and claims priority to IT Application No. RM2008A000497 filed Sep. 17, 2008, the entire contents of each of which are hereby incorporated by reference.

DESCRIPTION

The present invention refers to the field of veterinary medicine and in particular to a method for the diagnosis in vitam of Proventricular Dilatation Disease (PDD).

BACKGROUND OF THE INVENTION

Proventricular Dilatation Disease (PDD) occurs in several bird species (for example psittaciformes, accipitridiformes, columbiformes, anseriformes) and in particular in parrots (psittacides) wherein the disease is often fatal. Even if the disease was discovered three decades ago, its etiopathogenesis is still unclear.

Proventricular Dilatation Disease (PDD) was disclosed for the first time in the USA at the end of '70 in the genus Ara. Nowadays it is worldwide widespread, and it is observed in more than 50 species of psittacides, but also in Canadian gooses and in some birds of prey, but with very low frequency.

After several years form the discovery of PDD and in spite of the several study groups around the world, the etiologic agent is still un-isolated and un-clarified, even if the most acknowledged agent is a neurotropic virus, such as Paramyxovirus, and, in the last months, Bornavirus.

The disease shows two main types of symptoms: gastrointestinal disorders (undigested food in feces, regurgitation, and weight loss) and central nervous system disorders (tremors, instability, in-coordination, loss of balance), both presenting polyneuritis at a histological level and both often leading to death.

Besides the fragmentary knowledge on etiology, also the therapeutic protocol is incomplete. FANS are the top grade class of drugs used and they give unsatisfactory, and not resolving at long term, therapeutic results.

Nowadays, the in vitam methods for the diagnosis of Proventricular Dilatation Disease (PDD) are: endoscopy, radiography and biopsy.

Even if so many diagnostic tests are available, the only reliable method is biopsy, but it is poor sensible (40% of false negative) and it is dangerous for the subject undergoing to examination.

Nowadays, the diagnostic methods known in the art are all quite invasive and require the subject to be anesthetized, and thus they are risky and expensive for the animal's owner. At the same time, said methods do not give a definitive diagnosis since they cannot distinguish with absolute certainty between healthy and suffering subjects. In addition, they need surgical and stressful operations to be performed on the subjects undergoing to examination, which are at risk of death when they are already wasted by the disease.

Up until few years ago, Proventricular Dilatation Disease—PDD was poorly present and widespread in Italy, but frequently disclosed internationally. Now, the disease is occurring with a higher frequency and indistinctly affecting several species of parrots having different economic values.

Rarely the disease affects animals with a commercial value of around few tens of Euros, while it mainly affects Australian or South-Americans parrots of big size and high economic value (many tens of thousands of Euros) causing severe commercial losses and hardly damaging the worldwide commerce of said species.

Furthermore, an other aspect to be considered is that the disease can affect rare species of psittaciformes which count few tens of individuals (Spix's Macaw) and can further reduce the number of animals.

TECHNICAL PROBLEM

In view of the preponderance of the disease, the severe economic damage at a national and international level, and the threat for the species at risk of extinction, there is a strong felt need in the field for a diagnostic method which, contrary to the techniques already known in the art, is specific, less invasive, less expensive, easy to handle and to practice by the professional in hospitals, laboratories and outpatient clinics and with high sensibility and specificity.

SUMMARY OF THE INVENTION

Has now been found that the detection of specific anti-nervous system ganglioside antibodies in blood of subjects affected by Proventricular Dilatation Disease (PDD) is a reliable diagnostic method.

It has now been found that gangliosidic antigens isolated from the peripheral nervous system (PNS) and central nervous system (CNS) of parrots trigger the antibody response allowing said diagnosis.

Is therefore object of the present invention a ganglioside isolated from the peripheral nervous system (PNS) of a bird, preferably selected from the group consisting of psittaciformes, accipitridiformes, columbiformes e anseriformes, more preferably a parrot, also suffering from Proventricular Dilatation Disease (PDD).

An other object of the present invention is a ganglioside isolated from the central nervous system (CNS) of a bird, preferably selected from the group consisting of psittaciformes, accipitridiformes, columbiformes e anseriformes, more preferably a parrot, also suffering from Proventricular Dilatation Disease (PDD).

According to the present invention antigen means both the above mentioned ganglioside and a mixture of gangliosides isolated as above.

Object of the present invention is a ganglioside isolated from the central nervous system (CNS) of birds comprising at least one of the gangliosides selected from the group consisting of GD1a($C_{89}H_{157}N_3O_{39}$), GD1b ($C_{83}H_{145}N_3O_{39}$), GD3 ($C_{64}H_{113}N_3O_{29}$), GM2 ($C_{67}H_{119}N_3O_{26}$), GQ1b ($C_{106}H_{178}N_6O_{55}$) GalCer ($C_{40}H_{77}NO_8$), which may further comprise proteins as for example MAG (myelin-associated glycoprotein) and MBP (myelin basic protein $C_{74}H_{114}N_{20}O_{17}$).

A further object of the present invention is the use of the above gangliosides for the preparation of a medicament for the treatment of Proventricular Dilatation Disease and the pharmaceutical composition thereof.

A further object of the present invention is a method for the diagnosis of Proventricular Dilatation Disease in a subject comprising the detection, preferably by means of an ELISA assay, of an anti-ganglioside antibody in a body sample isolated from said subject.

A further object of the present invention is a method for the diagnosis of Proventricular Dilatation Disease in a subject comprising the steps of a) coating the antigen object of the present invention on a plate; b) blocking; c) adding the primary antibody followed by incubation and washing; d) incubation with the peroxidase-conjugated secondary antibody e) development; f) absorbance measurement.

An other object of the present invention is a method for the diagnosis of Proventricular Dilatation Disease comprising the steps of: a) coating the antigen object of the present invention on a plate; b) blocking; c) fixing and stabilizing the antigen in the darkness, with stirring, in the presence of 1% BSA and washing with PBST; d) adding the primary antibody followed by incubation and washing; e) adding a solution including BSA and polyvinylpyrrolidone in TBS, and normal serum from the animal species from which the secondary antibody derives and washing; f) incubation with the peroxidase-conjugated secondary antibody; g) development; h) absorbance measurement.

A further object of the present invention is a diagnostic kit for the detection of Proventricular Dilatation Disease comprising means for performing an ELISA assay, wherein the antigen is the ganglioside of the present invention.

An other object of the present invention is a diagnostic kit for the detection of Proventricular Dilatation Disease comprising means for performing one of the methods as above disclosed.

All the previously disclosed kits may further comprise bovine GM1 ganglioside and bovine GT1b ganglioside.

Further features of the present invention will be clearly evident from the following detailed description with reference to the examples.

DETAILED DESCRIPTION OF THE INVENTION

As previously discussed the methods known in the art are not able to clearly distinguish sick subjects from healthy subjects, and do not allow to come to a definitive diagnosis. Furthermore, the subjects under investigation need to be anesthetized whereupon they are risk of death when they are already wasted by the disease.

In addition, the surgical collection of bioptic tissue samples can worse an already critical clinical situation.

Thus, it is of great importance the development of a non-invasive serological test for the quick diagnosis of Proventricular Dilatation Disease (PDD).

A first object of the present invention is an antigen of ganglioside nature isolated from the peripheral nervous system (PNS) of birds, preferably *Psittacides*, more preferably parrots.

Said antigen is obtained by using a conventional method, for example as disclosed in C. K. Vorwerk "Ganglioside patterns in human spinal cord"—Spinal Cord (2001), 39, 628-632.

An other object of the present invention is an antigen of ganglioside nature isolated from the central nervous system (CNS) of birds, preferably *Psittacides*, more preferably parrots.

Said antigen is obtained by using a conventional method, for example as disclosed in C. K. Vorwerk "Ganglioside patterns in human spinal cord"—Spinal Cord (2001), 39, 628-632.

It is known that in the central nervous system, are present some gangliosidic fractions, especially GM1, GM1b, GD1a, GalNAc-GD1a, GD1b, GD3, GM2, GP1c, GQ1b, GalCer, and also some myelin proteic fractions such as MAG (myelin-associated glycoprotein) and MBP proteins (myelin basic proteins). Gangliosides form central nervous system (CNS) are quantitatively and qualitatively different from peripheral nervous system (PNS). (Gangliosides and Glycosphingolipids of Peripheral Nervous System Myelins—a Minireview. K. Ogawa-Goto and T. Abe. Neurochem Res. 1998 March; 23(3):305-10). In fact, some gangliosidic fractions, in particular GM1, GM1b, GD1a, GalNAc-GD1a, GD1b, GD3, GM2, GP1c, GQ1b, GalCer, but also myelin proteic fractions such as MAG (myelin-associated glycoprotein) and MBP proteins (myelin basic proteins) are mainly present.

The gangliosidic antigen obtained from the central nervous system (CNS) is particularly enriched of GD1a ($C_{89}H_{157}N_3O_{39}$), GD1b ($C_{83}H_{145}N_3O_{39}$), GD3 ($C_{64}H_{113}N_3O_{29}$), GM2 $C_{67}H_{119}N_3O_{26}$), GQ1b ($C_{106}H_{178}N_6O_{55}$) GalCer ($C_{40}H_{77}NO_8$).

In an embodiment of the present invention, said mixture further comprises proteins such as, for example, MAG (myelin-associated glycoprotein) and MBP (myelin basic protein $C_{74}H_{114}N_{20}O_{17}$).

Has been demonstrated by the same inventors that the use of the mixture isolated from the central nervous system (CNS) renders the method for the diagnosis of PDD more sensitive.

The method object of the present invention and the diagnostic kit thereof can be used in the outpatient clinic, in order to obtain the diagnosis on subjects suffering from the disease, soon before they show severe neurological lesions that lead to death, and thus to immediately start a suitable therapy.

The kit object of the present invention can be put into practice using common means for performing serological analysis with the ELISA assay. Said assay is known to the person skilled in the art, as an example Lequin R (2005). "Enzyme immunoassay (EIA)/enzyme-linked immunosorbent assay (ELISA).". *Clin. Chem.* 51 (12): 2415-8; Wide L, Porath J. Radioimmunoassay of proteins with the use of Sephadex-coupled antibodies. Biochem Biophys Acta 1966; 30:257-260; Engvall E, Perlman P (1971). "Enzyme-linked immunosorbent assay (ELISA). Quantitative assay of immunoglobulin G". *Immunochemistry* 8 (9): 871-4; Van Weemen B K, Schuurs A H (1971). "Immunoassay using antigen-enzyme conjugates.". *FEBS Letters* 15 (3): 232-6. In a preferred embodiment, the kit comprises further commercially available gangliosidic antigens, as for example, bovine GM1 $C_{73}H_{131}N_3O_{31}$ and bovine GT1b $C_{95}H_{195}N_5O_{49}$ from SIGMA-ALDRICH, preferably dissolved in ethanol.

Generally, the antigen of the present invention, represented by the ganglioside, in a suitable buffer volume, for example PBS pH 7,2 (phosphate buffer saline), is coated on a plate. Coating conditions are known in the field.

After washing the plate, a conventional blocking is performed.

The primary antibody, being the serum from the tested subject such as a parrot, from the negative control subject and from the positive control (anti-ganglioside antibody) is inserted into the wells. After conventional incubation and appropriate washing, incubation with the chicken anti IgG peroxidase-conjugated secondary antibody is performed, rabbit anti IgG peroxidase-conjugated antiserum as positive control is used. Development is performed according known techniques, and, at the end, absorbance is measured.

In a further embodiment, the kit object of the present invention, the serological analysis is performed by means of a modified and optimized ELISA assay wherein after the conventional blocking a further step was added in order to optimize the plate preparation wherein the antigen is fixed and the plate is stabilized in the darkness, with stirring, in the presence of 1% BSA (bovine serum albumine+PBS) and repeatedly washed with PBST, and after the addition of the primary antibody and the conventional incubation and washing but before adding the secondary antibody a further step was inserted in order to reduce the background, being quite high in this type of assay because gangliosides or glycoproteins (such as immunoglobulins) easily and aspecifically adsorb on the polystyrenic support of the plate, wherein a solution comprising BSA and polyvinylpyrrolidone in TBS is added and followed by the addition normal serum from the animal species from which the secondary antibody derives and washing.

The invention further comprises conventional modifications which do not change the essential features of the invention and can be performed by the person skilled in the art.

The method and the kit thereof can be used in the sell and purchase of animals, when the veterinary is required by the parties involved to determinate the state of health of the animals. The demand is ever-increasing because the import of exotic birds from out of Europe is restricted while the trade between breeders inside Europe and Italy is improving.

The following examples further elucidate the invention.

EXAMPLE 1

300 parrots from different species were tested for PDD in 12 big Italian private avian collections. The animals were anesthetized. Two bioptic samples from crop and plasma were collected from each parrot. Serial crop histological sections were stained with haematoxylin/eosin for morphologic evaluation. Two further staining with luxol fast blue—LFB and Dane & Hermann for mucins were performed.

PCNA antibodies (pAb, SANTACRUZ), anti-CD3 antibodies (mAb, SEROTEC), anti macrophages antibodies (mAb SEROTEC) and anti-CD8 antibodies (mAb, VMRD) were used to evaluate the mitotic activity of the epithelial basal layer cells and to immuno-phenotyping the inflammatory infiltrate.

The histological results and the serological results obtained with the well known ELISA assay and DotBlot and with a mixture of three new selected PDD antigens were correlated each other.

The results showed a high percentage of CD3+ lymphocytes, with large presence of plasma cells and macrophages in the perigangliar infiltrates. Early infiltrates of healthy animals showed few CD8+ cells and macrophages and spreading CD3+ T cells. A high percentage of CD8+ lymphocytes and macrophages were associated to moderate to severe perigangliar infiltrates.

In the last case, LFB staining showed demyelination. A high percentage of PCNA+ cells were detected in the basal crop epithelium of affected animals independently from the severity of the disease. Samples stained with DHTS showed differences in thickness of crop superficial pre-keratinized layer, between affected and non affected animals, being the thickness reduced in the affected animals.

Histology confirmed the suppurative ganglioneuritis, with gliosis, demyelination and ganglia swelling.

EXAMPLE 2

1 absolute microgram of antigen, being the ganglioside, in 100 microliter of PBS pH 7,2 (phosphate buffer saline), undergoes to coating overnight at +4° C. on Nunc plate (Maxisorp 96 wellf DK).

After, the plate is washed three times with PBST (PBS, TWEEN 20 0.01%) with 200 microliters each single well, the blocking is performed with 200 microliters PBST, 1% BSA (bovine serum albumin), for one hour in the darkness at room temperature with stirring, at the end washed three times with PBST. The primary antibody, being the serum of the parrot under examination in 100 microliters of PBS pH 7,2, the serum of the negative control parrot diluted 1:50, the positive control (antiganglioside antibody) diluted 1:3000 is added into the wells, incubated for one hour at 37° C., washed three times with PBST (PBS, TWEEN 20 0.01%) 200 microliters each single well. Afterwards the serum under examination and the negative control are incubated with a chicken anti IgG peroxidase-conjugated secondary antibody (SIGMA), rabbit anti IgG peroxidase-conjugated antiserum (SIGMA) diluted 1:2500 in PBS is used as a positive control. Incubation last for 90 minutes in the darkness at room temperature and washed three times with PBST. The development is performed in 100 microliters ABTS SIGMA (peroxidase substrate) for 30 minutes at room temperature. Peroxidase activity is blocked by adding 100 microliters of 1% SDS (sodium dodecyl sulphate). Absorbance is measured at 405 nm with an ELISA reader MULTISKAN ASCENT LABSISTEMS.

The histological results compared with the serological result show a correlation of around 90%.

EXAMPLE 3

Six mixtures of purified ganglioside, intraperitoneally and orally administered together with suitable adjuvants, were tested. 2 weeks after administration, the 100% of the subjects undergoing to intraperitoneal administration and the 33% of the subject undergoing to oral administration developed typical symptoms. 4 mixtures showed typical ganglioneuritis in the crop biopsy.

These findings, together with immunotyping suggest an autoimmune mechanism for PDD.

In view of these results the method for detecting PDD was developed.

EXAMPLE 4

In each well of the ELISA plate 1 microgram of antigen in 100 microliters of PBS pH 7,2 (phosphate buffer saline) is absorbed overnight (12 hours) at a temperature of 4° C. The antigen, depending on the antiganglioside antibody to be detected in the sample under examination, is made of bovine ganglioside Gm1 $C_{73}H_{131}N_3O_{31}$ in methanol, bovine ganglioside Gt1b $C_{95}H_{195}N_5O_{49}$ in ethanol, or gangliosidic extract from avian central nervous system in methanol.

Afterwards, every single well is washed three times with 200 microliters of 0,01% PBST (phosphate buffer saline +TWEEN 20). Soon after the antigen is fixed and the plate stabilized for 1 hour in the darkness with stirring, with 200 microliters of BSA 1% (bovine serum albumine+PBS) and washed again three times with PBST. At this stage, 100 microliters of: Gm1 anti-ganglioside antibody or Gt1b anti-ganglioside antibody diluted 1:5000 in PBS, or plasma of parrot suffering from PDD diluted 1:50 in PBS, in the wells used as positive controls, 100 microliters of plasma of a healthy subject diluted 1:50 in PBS used as negative control and 100 microliters of plasma of the parrot under examination diluted 1:50 in PBS; incubated for three hours at 37° C. and at the end of the incubation, washed three times with PBST.

After conventional washing, 100 microliters of a solution containing 1% BSA and 1% polyvinylpyrrolidone (PVP) both in TBS (Tris buffer solution) are positioned in each well and normal serum from the normal serum from the animal species from which the secondary antibody derives (rabbit in the present case) at a dilution of 1:100 is added. Said mixture is maintained into the wells at room temperature for 15 minutes; after a quick washing the peroxidised secondary antibody is added. Soon after 100 microliters of peroxidised secondary antibody are added, it is a bovine anti IgG antibody diluted 1:2500 in PBS as positive control, while as negative control, as positive control it is a Rabbit-anti chicken IgG diluted in 1:2500 in PBS. The secondary antibody is incubated in the darkness for 90 minutes at room temperature under continuous stirring; after 90 minutes is washed three times with PBST. At the end, for a time of 30 minutes, 100 microliters of ABST (SIGMA), previously diluted at room temperature, are added. At the end of this period of time, peroxidase activity is blocked by adding 100 microliters of 1% SDS. After three minutes the measurement is carried out with a spectrophotometer at 405 nm. The sample under examination is positive when the value of OD (optical density) of said sample is grater than the average mean between the positive and the negative values, both deducted of the blank value (obtained from the wells without primary and secondary antibodies); likewise, if the examined value is not greater that said average means the sample is considered negative.

EXAMPLE 5

800 serum samples collected from 23 genus of parrots where investigated and, in 140 cases, in the same parrot the histological aspect of the crop biopsy was compared with the serological antibody titre. It has been shown that in the 98% of examined cases at least one of the three tested antigens was positive (single bovine gangliosides or a mixture of gangliosides from the central nervous system of parrot) and more than 70% of histological positive cases showed antibody titres, of all the three tested antigens, higher than the threshold value.

BIBLIOGRAPHY

Gerlach S. 1991. Macaw wasting disease—a 4-year study on clinical cases, history, epizootiology, analysis of species, diagnosis and differential diagnosis, microbiological and virological results. Proc Ann Conf European Chap Assoc Avian Vet, pp. 273-281.

Graham D L. 1984. Infiltrative splanchnic neuropathy: a component of the wasting macaw complex? Proc Internatl Conf Avian Med, p. 275.

Mannl A, Gerlach H, Leipold R. 1987. Neuropathic gastric dilatation in psittaciformes. Avian Dis 31: 214-221.

Phalen D N. 1986. An outbreak of psittacine proventricular dilatation syndrome (PPDS) in a private collection of birds and an atypical form of PPDS in a nanday conure. Proc Ann Conf Assoc Avian Vet, pp. 27-34.

Rosskopf W J, Woerpel R W, Reed-Blake S. 1986. Pet avian conditions and syndromes—an update. Proc Ann Conf Assoc Avian Vet, pp. 377, 392-393, 399.

Cazayoux-Vice C A. 1992. Myocarditis as a component of psittacine proventricular dilatation syndrome in a Patagonian conure. Avian Dis 36: 1117-1119.

Clark F D. 1984. Proventricular dilatation syndrome in large psittacine birds. Avian Dis 28: 813-815.

Degernes L A, Flammer K, Fisher P. 1991. Proventricular dilatation syndrome in a green-winged macaw. Proc Annl Conf Assoc Avian Vet, pp. 45-49.

Graham D L. 1991. Wasting/proventricular dilatation disease: A pathologist's view. Proc Ann Conf Assoc Avian Vet, pp. 43-44.

Hughes P E. 1984. The pathology of myenteric ganglioneuritis, psittacine encephalomyelitis, proventricular dilatation of psittacines, and macaw wasting syndrome. Proc 33rd Western Poult Dis Conf, pp. 85-87.

Joyner K I, Kock N, Styles D. 1989. Encephalitis, proventricular and ventricular myositis, and myenteric ganglioneuritis in an umbrella cockatoo. Avian Dis 33: 379-381.

Lutz M E, Wilson R B. 1991. Psittacine proventricular dilatation syndrome in an umbrella cockatoo. J Am Vet Med Assoc 198: 1962-1963.

Malley D M. 1991. Case report: a case study of a Moluccan cockatoo with proventricular dilatation. Proc Ann Conf European Chap Assoc Avian Vet, pp. 271-272.

Rich G. 1992. Classic and atypical cases of proventricular dilatation disease. Proc Ann Conf Assoc Avian Vet, pp. 119-125.

Ridgeway R A, Gallerstein G A. 1983. Proventricular dilatation in psittacines. Proc Ann Conf Assoc Avian Vet, pp. 228-230.

Spenser E L. 1991. Common infectious diseases of psittacine birds seen in practice. Vet Clin N Am: Small Anim Pract 21: 1227.

Suedemeyer W K. 1992. Diagnosis and clinical progression of three cases of proventricular dilatation syndrome. J Assoc Avian Vet 6: 159-163.

Turner R. 1984. Macaw fading or wasting syndrome. Proc 33rd Western Poult Dis Conf, pp. 87-88.

Woerpel R W, Rosskopf W J. 1984. Clinical and pathological features of macaw wasting disease (proventricular dilatation syndrome). Proc 33rd Western Poult Dis Conf, pp. 89-90.

Gregory C R, Latimer K S, Campagnoli R P, Ritchie B W. 1996. Histologic evaluation of the crop for diagnosis of proventricular dilatation syndrome in psittacine birds. J Vet Diagn Invest 8: 76-80.

Bond M W, Downs D, Wolf S. 1993. Screening for psittacine proventricular dilatation syndrome. Proc Ann Conf Assoc Avian Vet, pp. 92-97.

Rosskopf W J, Woerpel R W, Reed-Blake S. 1985. Pet avian disease syndromes. Proc Ann Conf Assoc Avian Vet, pp. 299-317.

Gregory C R, Latimer K S, Niagro F D, Roberts A W, Campagnoli R P, Pesti D A, Ritchie B W, Lukert P D. 1997. Investigations of Eastern equine encephalomyelitis virus as the causative agent of psittacine proventricular dilation syndrome. J Avian Med Surg 11: 187-193.

Woerpel R J, Rosskopf W J, Hughes E. 1984. Proventricular dilatation and wasting syndrome: myenteric ganglioneuritis and encephalomyelitis of psittacines; an update. Proc Internatl Conf Avian Med, pp. 25-28.

Gregory C R, Latimer K S, Niagro F D, Campagnoli R P, Ritchie B W, Steffens W L. 1996. Characterization of virus-like particles from tissues of birds diagnosed with proventricular dilatation syndrome (PDS). Proc Animal Dis Res Workers in Southern States, p. 25.

Gough R E, Drury S E, Harcourt-Brown N H. 1996. Virus-like particles associated with macaw wasting disease. Vet Rec 139: 24.

Uncini, A, Lugaresi, A. Fisher syndrome with tetraparesis and antibody to GQ1b: evidence for motor nerve terminal block. Muscle Nerve 1999. 22:640-644.

Dullforce, P, Sutton, D C, Heath, A W. Enhancement of T cell-independent immune responses in vivo by CD40 antibodies. Nat Med 1998. 4:88-91.

Willison, H J, Veitch, J. Immunoglobulin subclass distribution and binding characteristics of anti-GQ1b antibodies in Miller Fisher syndrome. J Neuroimmunol 1994. 50:159-165.

R. A. C. Hughes, R. D. M. Hadden, N. A. Gregson and K. J. Smith, Pathogenesis of Guillain-Barré syndrome. J. Neuroimmunol. 100 (1999), pp. 74-97.

M. Carpo, R. Pedotti, S. Allaria et al., Clinical presentation and outcome of Guillain-Barré and related syndromes in relation to anti-ganglioside antibodies. J. Neurol. Sci. 168 (1999), pp. 78-84.

K. Ogawara, S. Kuwabara, M. Mori et al., Axonal Guillain-Barré syndrome: relation to anti-ganglioside antibodies and *Campylobacter jejuni* infection in Japan. Ann. Neurol. 48 (2000), pp. 624-631.

R. Press, S. Mata, F. Lolli, J. Zhu, T. Andersson and H. Link, Temporal profile of anti-ganglioside antibodies and their relation to clinical parameters and treatment in Guillain-Barré syndrome. J. Neurol. Sci. 190 (2001), pp. 41-47.

T. W. Ho, H. J. Willison, I. Nachamkin et al., Anti-GD1a antibody is associated with axonal but not demyelinating forms of Guillain-Barré syndrome. Ann. Neurol. 45 (1999), pp. 168-173.

N. Yuki, Y. Tagawa, F. Irie et al., Close association of Guillain-Barré syndrome with antibodies to minor monosialogangliosides GM1b and GM1a. J. Neuroimmunol. 74 (1997), pp. 30-34.

A. A. Ilyas, S. D. Cook, F. A. Mithen et al., Antibodies to GT1a ganglioside in patients with Guillain-Barré syndrome. J. Neuroimmunol. 82 (1998), pp. 160-167.

M. Carpo, R. Pedotti, F. Lolli et al., Clinical correlate and fine specificity of anti-GQ1b antibodies in peripheral neuropathy. J. Neurol. Sci. 155 (1998), pp. 186-191.

K. Yako, S. Kusunoki and I. Kanazawa, Serum antibody against a peripheral nerve myelin ganglioside, LM1, in Guillain-Barré syndrome. J. Neurol. Sci. 168 (1999), pp. 85-89.

A. Alaedini and N. Latov, Ganglioside agglutination immunoassay for rapid detection of autoantibodies in immune-mediated neuropathy. J. Clin. Lab. Anal. 15 (2001), pp. 96-99.

A. K. Asbury and D. R. Cornblath, Assessment of current diagnostic criteria for Guillain-Barré syndrome. Ann. Neurol. 27 (1990), pp. S21-S24.

T. W. Ho, B. Mishu, C. Y. Li et al., Guillain-Barré syndrome in northern China: relationship to *Campylobacter jejuni* infection and anti-glycolipid antibodies. Brain 118 (1995), pp. 597-605.

M. Odaka, N. Yuki and K. Hirata, Anti-GQ1b IgG antibody syndrome: clinical and immunological range. J. Neurol. Neurosurg. Psychiatry 70 (2001), pp. 50-55.

M. Koga, M. Tatsumoto, N. Yuki and K. Hirata, Range of cross reactivity of anti-GM1 IgG antibody in Guillain-Barré syndrome. J. Neurol. Neurosurg. Psychiatry 71 (2001), pp. 123-124.

A. van Belkum, N. van den Braak, P. Godschalk et al., A Campylobacter jejuni gene associated with immune-mediated neuropathy. Nat. Med. 7 (2001), pp. 752-753.

E. Bech, T. F. Orntoft, L. P. Andersen and J. Jakobsen, IgM anti-GM1 antibodies in the Guillain-Barré syndrome: a serological predictor of the clinical course. J. Neuroimmunol. 72 (1997), pp. 59-66.

S. Kuwabara, N. Yuki, M. Koga et al., IgG anti-GM1 antibody is associated with reversible conduction failure and axonal degeneration in Guillain-Barré syndrome. Ann. Neurol. 44 (1998), pp. 202-208.

N. Yuki, M. Yamada and S. Sato, Association of IgG anti-GD1a antibody with severe Guillain-Barré syndrome. Muscle Nerve 16 (1993), pp. 642-647.

M. Carpo, E. Nobile-Orazio, N. Meucci et al., Anti-GD1a ganglioside antibodies in peripheral motor syndromes. Ann. Neurol. 39 (1996), pp. 539-543.

T. W. Ho, H. J. Willison, I. Nachamkin et al., Anti-GD1a antibody is associated with axonal but not demyelinating forms of Guillain-Barré syndrome. Ann. Neurol. 45 (1999), pp. 168-173.

R. Dabby, L. H. Weimer, A. P. Hays, M. Olarte and N. Latov, Antisulfatide antibodies in neuropathy: clinical and electrophysiologic correlates. Neurology 54 (2000), pp. 1448-1452.

A. A. Ilyas, F. A. Mithen, M. C. Dalakas et al., Antibodies to sulfated glycolipids in Guillain-Barré syndrome. J. Neurol. Sci. 105 1 (1991), pp. 108-117 Sep.

A. Chiba, S. Kusunoki, H. Obata, R. Machinami and I. Kanazawa, Serum anti-GQ1b IgG antibody is associated with ophthalmoplegia in Miller Fisher syndrome and Guillain-Barré syndrome: clinical and immunohistochemical studies. Neurology 43 (1993), pp. 1911-1917.

M. Ogino, N. Orazio and N. Latov, IgG anti-GM1 antibodies from patients with acute motor neuropathy are predominantly of the IgG1 and IgG3 subclasses. J. Neuroimmunol. 58 (1995), pp. 77-80.

H. J. Willison and J. Veitch, Immunoglobulin subclass distribution and binding characteristics of anti-GQ1b antibodies in Miller Fisher syndrome. J. Neuroimmunol. 50 (1994), pp. 159-165.

M. Carpo, R. Pedotti, S. Allaria et al., Clinical presentation and outcome of Guillain-Barré syndrome and related syndromes in relation to anti-ganglioside antibodies. J. Neurol. Sci. 168 (1999), pp. 78-84.

S. Kuwabara, N. Yuki, M. Koga et al., IgG anti-GM1 antibody is associated with reversible conduction failure and axonal degeneration in Guillain-Barré syndrome. Ann. Neurol. 44 (1998), pp. 202-208.

The invention claimed is:

1. A method for the diagnosis of Proventricular Dilatation Disease in a subject comprising determining an anti-ganglioside antibody isolated from the central nervous system (CNS) of birds in a body sample isolated from said subject wherein the presence of the anti-ganglioside antibody indicates that the subject has a Proventricular Dilatation Disease.

2. A method for the diagnosis of Proventricular Dilatation Disease in a subject comprising the following steps:
   a) coating an antigen from a ganglioside isolated from the central nervous system (CNS) of birds on a plate;
   b) blocking;
   c) adding a primary antibody, incubating and washing;
   d) incubating with a peroxidase-conjugated secondary antibody;
   e) developing; and
   f) measuring absorbance to determine the presence of the peroxidase-conjugated secondary antibody;
   wherein the presence of an anti-ganglioside antibody indicates that the subject has a Proventricular Dilatation Disease.

3. A method for the diagnosis of Proventricular Dilatation Disease in a subject comprising the following steps:
   a) coating an antigen from a ganglioside isolated from the central nervous system (CNS) of birds on a plate;
   b) blocking;
   c) fixing and stabilizing the antigen in darkness, with stirring, in the presence of 1% bovine serum albumin and washing with phosphate buffered saline/TWEEN;
   d) adding a primary antibody, incubating and washing;
   e) adding a solution containing bovine serum albumin and polyvinylpyrrolidone dissolved in Tris buffered saline, and normal serum from the animal species from which the secondary antibody derives and washing;

f) incubating with peroxidase-conjugated secondary antibody;

g) developing; and h) measuring absorbance to determine the presence of the peroxidase-conjugated secondary antibody;

wherein the presence of an anti-ganglioside antibody indicates that the subject has a Proventricular Dilatation Disease.

* * * * *